United States Patent [19]

Nakahara et al.

[11] 4,226,991
[45] Oct. 7, 1980

[54] PROCESS FOR PREPARING 3-ALKYLTHIOPROPIONIC ACID ESTERS

[75] Inventors: Yutaka Nakahara, Iwatsuki; Tohru Haruna, Okegawa; Kenji Tazima, Kuwana, all of Japan

[73] Assignee: Argus Chemical Corp., Brooklyn, N.Y.

[21] Appl. No.: 950,976

[22] Filed: Oct. 13, 1978

[30] Foreign Application Priority Data

Oct. 17, 1977 [JP] Japan ................. 52/125007

[51] Int. Cl.$^2$ ........................... C07D 251/34
[52] U.S. Cl. .................... 544/221; 560/152; 260/45.8 NT; 260/45.85 H
[58] Field of Search ............ 544/221; 560/152

[56] References Cited

U.S. PATENT DOCUMENTS

| | | | |
|---|---|---|---|
| 3,683,048 | 8/1972 | Kolyer et al. | 544/221 |
| 3,707,542 | 12/1972 | Steinberg et al. | 544/221 |
| 3,708,543 | 1/1973 | Hickner et al. | 560/152 |
| 3,741,909 | 6/1973 | Yamane et al. | 562/512 |
| 3,758,549 | 9/1973 | Dexter et al. | 560/152 |
| 4,125,516 | 11/1978 | Dexter et al. | 544/221 |

FOREIGN PATENT DOCUMENTS 50-106881 8/1975 Japan ........................ 544/221

Primary Examiner—Henry R. Jiles
Assistant Examiner—Jane T. Fan
Attorney, Agent, or Firm—Otto S. Kauder

[57] ABSTRACT

A new process for preparing a polyhydric alcohol 3-alkyl-thiopropionate polyolefin resin stabilizer is provided, in which there is heated a reaction mixture containing a polyhydric alcohol, an alpha-olefin having 6 to 40 carbon atoms, and betamercaptopropionic acid or a lower alkyl betamercaptopropionate in the presence of an organic peroxide or azonitrile reaction initiator, and the polyhydric alcohol 3-alkylthiopropionate polyolefin resin stabilizer is recovered from the mixture.

Polyolefin resin compositions stabilized with the stabilizer prepared by the process of this invention, and stabilizer compositions comprising the stabilizer prepared by the process of this invention together with a phenol and/or an alkaline earth metal salt of a monocarboxylic acid are also provided.

12 Claims, No Drawings

PROCESS FOR PREPARING 3-ALKYLTHIOPROPIONIC ACID ESTERS

BACKGROUND OF THE INVENTION

This invention relates to a new process for the preparation of polyhydric alcohol 3-alkylthiopropionate ester stabilizers for polyolefin resins. Polyhydric alcohol 3-alkylthiopropionate ester stabilizers have been disclosed previously, but their preparation conventionally has required the use of relatively costly starting materials and furnished products that when used to stabilize polyolefin resins have contributed to the formation of undesirable yellowish and beige discolorations as well as unpleasant odors when the stabilized resins were processed or heat aged at elevated temperatures.

Thioether carboxylic acid esters and their use for stabilizing polymers have been discussed by M. Minagawa et al, in U.S. Pat. No. 4,106,629 of Aug. 8, 1978, and for the sake of brevity it is sufficient here to refer to Minagawa's discussion of this art.

Trihydric and higher valent polyhydric alcohol 3-alkylthiopropionate ester stabilizers have conventionally been prepared as disclosed, for example, by M. Dexter in U.S. Pat. No. 3,758,549 of Sept. 11, 1973 by reaction of a polyhydric alcohol such as pentaerythritol with methyl 3-laurylthiopropionate by transesterification and subsequent purification of the product, such as by chromatography on a column of alumina. Dexter disclosed the preparation of the required 3-alkylthiopropionic acid ester intermediate by reaction of the alkyl mercaptan with methyl acrylate and purification of the intermediate by high vacuum distillation, so that Dexter's process comprises two synthetic steps ad two purification steps that present considerable difficulty in commercial scale operation.

M. Minagawa in Japanese Kokai No. 75/106881 of Aug. 27, 1975 disclosed stabilized resin compositions containing 3-alkylthiopropionate esters of alcohols containing a nitrogen-heterocyclic ring, for example tris(2-hydroxyethyl isocyanurate) and optionally a phenolic antioxidant.

Minagawa's esters are shown as synthesized by esterification of the nitrogen-heterocyclic alcohol with a 3-alkylthiopropionic acid, without a suggestion of how the required 3-alkylthiopropionic acid intermediates were to be obtained.

Disclosures of the preparation of 3-alkylthiopropionic acids, their lower alkyl esters, and their metal salts include M. Gribbins U.S. Pat. No. 2,416,052 of Feb. 15, 1947, who added mercaptans to acrylonitrile followed by acid or alkaline hydrolysis of the nitrile group; W. Leistner in U.S. Pat. Nos. 2,680,107 of June 1, 1954 and 2,723,965 of Nov. 15, 1955, who added alkyl mercaptan to methyl acrylate with sodium methylate catalyst, hydrolyzed the resulting methyl ester to the sodium salt of the acid by heating with NaOH, and then acidified to isolate the acid; and I. Yamane in U.S. Pat. No. 3,741,909 of June 26, 1973 who disclosed stable organic material prepared by mixing with a compound expressed by the general formula;

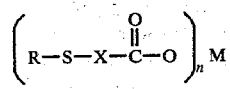

(wherein R represents hydrocarbon radical having 6-22 carbon atoms, X represents a lower alkylene radical having 1-5 carbon atoms, M represents non-alkali metal and n represents an integer ranging from 1 to 5) along with a phenol-type antioxidant or amine-type antioxidant.

This compound is synthesized through the following process;

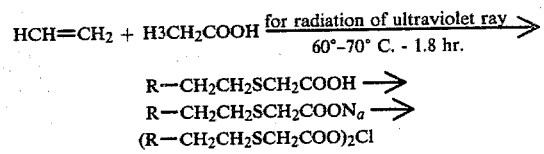

$R-CH_2CH_2SCH_2COOH \longrightarrow$
$R-CH_2CH_2SCH_2COON_a \longrightarrow$
$(R-CH_2CH_2SCH_2COO)_2Cl$

SUMMARY OF THE INVENTION

An object of this invention is to provide a simplified one-step process for preparing a polyhydric alcohol 3-alkylthiopropionic acid ester polyolefin resin stabilizer capable of stabilizing the resin against oxidative degradation for a long period of time.

Another object of this invention is to obtain a polyhydric alcohol 3-alkylthiopropionic acid ester having a high polyolefin resin stabilizing effect with no need of undergoing extensive or repeated purification steps.

In accordance with this invention, a polyhydric alcohol 3-alkylthiopropionate polyolefin resin stabilizer capable of enhancing the resistance to deterioration and minimizing the formation of undesirable color and odor of a polyolefin resin when heated at 150° C. and higher is prepared by heating a reaction mixture containing at least one polyhydric alcohol having 3 to 6 alcoholic hydroxyl groups and 3 to 20 carbon atoms, provided that the number of carbon atoms is at least equal to the number of alcoholic hydroxyl groups, and for each mole of alcoholic hydroxyl group supplied by the polyhydric alcohol from 0.6 to 1.5 moles of a betamercaptopropionic acid compound selected from the group consisting of betamercaptopropionic acid and a lower alkyl ester thereof and from 0.6 to 2 moles of at least one alpha-olefin having 6 to 40 carbon atoms, and an amount effective to initiate reaction of a reaction initiator selected from the group of azonitriles and organic peroxides, and recovering the polyhydric alcohol 3-alkylthiopropionate polyolefin resin stabilizer from the reaction mixture. A preferred technique for recovering the stabilizer from the reaction mixture involves the use of a combination of solvents comprising an aromatic hydrocarbon boiling in the range of 80°-190° C. and a lower aliphatic alcohol, from which the stabilizer having the desired properties is obtained in excellent yield.

Polyolefin resins stabilized with the polyhydric alcohol 3-alkylthiopropionates prepared according to this invention are characterized by excellent heat stability, and retention of good color and odor properties, and include homopolymers and copolymers of alpha-olefins having 2 to 6 carbon atoms, especially polypropylene and polyethylene.

Excellent stabilizer compositions for polyolefin resins comprise the stabilizer prepared according to this invention together with at least one known polyolefin stabilizer, such as a phenol and/or an alkaline earth metal salt of a monocarboxylic acid having 6 to 24 carbon atoms. Such stabilizer compositions typically contain from 10 to 95 parts by weight of polyhydric alcohol 3-alkylthiopropionate prepared according to this invention, from 5 to 90 parts by weight of a phenol, and from zero to 50 parts by weight of alkaline earth metal salt.

DESCRIPTION OF THE PREFERRED EMBODIMENTS

The alpha-olefin starting materials for the process according to this invention all have the characteristic terminal =CH$_2$ group, and the carbon atom adjacent the terminal =CH$_2$ carries from 1 to 2 alkyl groups. Accordingly, the alpha-olefin can be represented by the formula RR'C=CH$_2$ in which R is an alkyl group, R' is an alkyl group or a hydrogen atom, and the sum of the number of carbon atoms in R and R' is from 4 to 38, preferably from 8 to 28. Useful alpha-olefins include, for example, hexene-1, 2-methylpentene-1, 4-methylpentene-1, heptene-1, octene-1, 2-ethylhexene-1, nonene-1, decene-1, 2,4,4-trimethylpentene-1, dodecene-1, hexadecene-1, eicosene-1, tetracosene-1, and octacosene-1.

The betamercaptopropionic acid compound can be represented by the formula HSCH$_2$CH$_2$CO$_2$R'' where R'' is a hydrogen atom or a lower alkyl group such as i-butyl, n-butyl, s-butyl, t-butyl, ethyl, isopropyl, methyl, and n-propyl.

Polyhydric alcohols used according to this invention have 3 to 6 alcoholic hydroxyl groups and 3 to 20 carbon atoms, but not more than one hydroxyl group linked to any one carbon atom.

Examples of polyhydric alcohols used according to this invention include trimethylolpropane, trimethylolethane, glycerin, tris(2-hydroxyethyl)isocyanurate, pentaerythritol, ditrimethylolpropane, dipentaerythritol, mannitol, sorbitol, inositol, etc.

The reaction initiator azonitrile or organic peroxide is used suitably in a concentration effective to initiate reaction of 0.001 to 5 percent by weight of the alpha-olefin and betamercaptopropionic acid compound combined, preferably 0.05 to 2 percent. Larger amounts of reaction initiator can be used but are wasteful and uneconomical.

Useful and preferred azonitrile initiators include 2,2'-azobis-(2-methylpropionitrile), 2,2'-azobis(2-methylbutyronitrile)-2,2'-azobis(2,4-dimethylvaleronitrile, and 1,1'-azobis(1-cyclohexanenitrile).

Useful organic peroxides have 1 to 2 peroxide (—OO—) groups and 4 to 40 carbon atoms and include t-alkyl and aralkyl peroxides such as t-butylhydroperoxide, cumyl-t-butyl peroxide, 2,5-dimethyl-2,5-di(t-butylperoxy)hexane, di-t-butylperoxide and dicumyl peroxide; monoperesters such as t-butyl peracetate, t-butylperoxyisobutyrate, t-butylperbenzoate, t-butylperpivalate, t-butylper-2-ethylhexoate, t-butylperoxyneodecanoate, t-butylperlaurate, and mono-t-butylperoxymaleic acid; diperesters such as 2,5-bis(2-ethylhexanoylperoxy)-2,5-dimethylhexane, di-t-butylperoxyphthalate, and 2,5-bis(benzoylperoxy)-2,5-dimethylhexane; aromatic diacyl peroxides such as 2,4-dichlorobenzoylperoxide, benzoyl peroxide and o-toluoylperoxide; Ketone peroxides such as methyl ethyl ketone peroxide, cyclohexanone peroxide, and 1,1-bis(t-butylperoxy)-3,3,3-trimethylcyclohexane; and peroxycarbonate esters such as di-sec-butylperoxydicarbonate, di-t-butylcyclohexylperoxydicarbonate and t-butylperoxyisopropoylcarbonate.

A particularly preferred group of organic peroxide initiators consists of aliphatic diacyl peroxides such as acetyl peroxide, acetylpropionyl peroxide, acetyl 2-ethylhexanoyl peroxide, 3,3,5-trimethylhexanoylperoxide, lauroyl peroxide, octanoyl peroxide, decanoyl peroxide, stearoyl peroxide, propionyl hexacosanoyl peroxide and succinic acid peroxide.

In the reaction of alpha-olefin with betamercaptopropionic acid compound and polyhydric alcohol the reacting proportions of the reactants are one double bond of an alpha-olefin with one SH group of a betamercaptopropionic acid compound, and one carboxylic acid or ester group derived from a betamercaptopropionic acid compound with one alcoholic hydroxyl group of a polyhydric alcohol.

In carrying out the reaction, the reactants can be mixed in these proportions, but it is sometimes advantageous to use an excess of one reactant and if desired remove and recover the unused portion of such reactant.

When the reactants are mixed in such proportions that there is a modest excess of betamercaptopropionic acid compound relative to the amount of alpha-olefin, or a modest excess of polyhydric alcohol relative to the amount of betamercaptopropionic acid compound, the product of the process of this invention can include unobjectionable and sometimes even beneficial minor amounts of constituents having free mercapto groups and/or alcoholic hydroxyl groups in addition to thioether and carboxylic ester groups. Accordingly, in carrying out the process of this invention the reactants can be mixed in proportions ranging from 0.6 to 1.5 moles of betamercaptopropionic acid compound and 0.6 to 2 moles of alpha-olefin per mole of alcoholic hydroxyl supplied by the polyhydric alcohol. A preferred range of proportions in which the reactants are mixed is from 0.9 to 1.1 moles of betamercaptopropionic acid compound and 0.9 to 1.1 moles of alpha-olefin per mole of alcoholic hydroxyl group.

The reaction is carried out at a temperature within the range of 20°–200° C., preferably 50° to 150° C.

Once initiated, the reaction of a polyhydric alcohol an alpha-olefin with a betamercaptopropionic acid compound is exothermic. One convenient way to control the reaction is to warm the polyhydric alcohol alpha-olefin and a quantity of the initiator to a temperature where reaction can be initiated, suitably 40°–60° C., remove the heat source, and add betamercaptopropionic acid compound at a rate such that the reaction is sustained until completed by the exothermic effect or by externally supplied heat if necessary.

Another useful method is to premix polyhydric alcohol, betamercaptopropionic acid compound, and alpha-olefin at 40°–60° C. and add quantities of reaction initiator from time to time with further heating as needed until analysis shows the consumption of mercaptopropionic acid compound to be complete. If desired, any unreacted starting materials can then be removed before continuing to the isolation of the desired product.

The reaction can be helped to completion by removal of the side product water or lower alkanol, by the use of an esterification catalyst, or by both of these expedients in combination. Water or lower alkanol produced during the esterification can be removed by distillation, assisted by application of vacuum, by sparging with a gas, or by the use of a boiling inert solvent. Esterification catalysts that can be used include organic sulfonic acids, inorganic acids, bases, and multivalent metal and organo metallic compounds, for example sulfuric acid, hydrochloric acid, boric acid, ethanesulfonic acid, sodium methoxide, potassium bicarbonate, zinc chloride, aluminum, titanium, and zirconium butoxides, dimethyltin dichloride, dibutyltin oxide, and di-n-octyltin oxide. As little as 0.001% of esterification catalyst is helpful, and up to about 5% can be utilized by weight of the reactants.

The polyhydric alcohol 3-alkylthiopropionate produced by the process of this invention can be isolated from the reaction mixture in which it is obtained by conventional techniques such as stripping of volatile reactants and by-products, suitably under reduced pressure, away from the desired product; crystallization from a suitable solvent, directly or after stripping; or separation from undesired impurities by enriching the desired product in one of a pair of immiscible liquids, for example the pair hexane and 80% aqueous methanol.

A particularly preferred and convenient method for recovering polyhydric alcohol 3-alkylthiopropionate according to this invention comprises the use of a solvent combination of an aromatic hydrocarbon having an atmospheric boiling point in the range from 80° to 190° C. and a lower aliphatic alcohol. Suitable aromatic hydrocarbons include benzene, toluene, ethylbenzene, o-, m-, and p-xylene, cumene, p-cymene, trimethylbenzenes, ethylmethylbenzenes, diethylbenzenes, and mixtures thereof. Suitable lower alcohols include the isomeric butyl, ethyl, methyl and propyl alcohols and mixtures thereof. An especially preferred solvent combination comprises toluene and methanol. the combined solvents can be used in admixture or sequentially, usually first the hydrocarbons and then the alcohol.

Illustrative polyhydric alcohol 3-alkylthiopropionates prepared by a process of this invention are shown by name and formula.

1,3,5-Tris(n-hexylthiopropionyloxyethyl isocyanurate

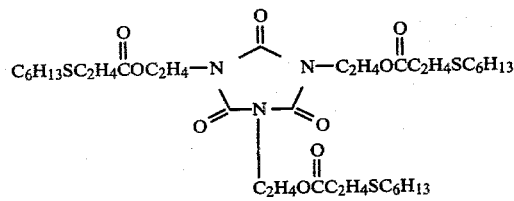

1,3,5-Tris(n-dodecylthiopropionyloxyethyl)isocyanurate

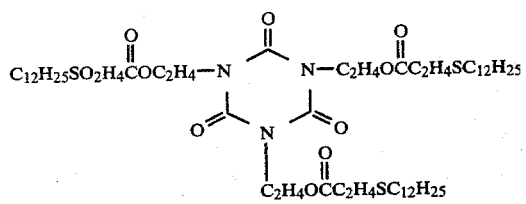

1,3-Bis(n-octadecylthiopropionyloxyethyl)-5-hydroxyethyl isocyanurate

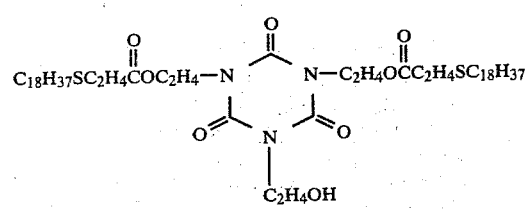

Pentaerythritol tetrakis (3-n-octylthiopropionate)

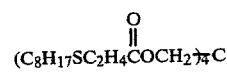

Pentaerythritol tetrakis (3-n-dodecylthiopropionate)

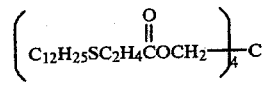

Pentaerythritol tetrakis(3-n-octadecylthiopropionate)

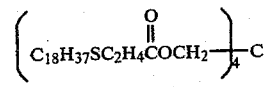

Pentaerythritol tris(3-n-docosanylthiopropionate)

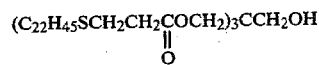

Glyceryl tris(n-decylthiopropionate)

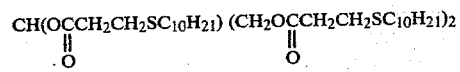

Glyceryl mono(3-n-hexadecylthiopropionate)

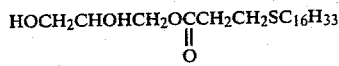

Examples 1 through 6 below provide illustrative and non-limiting detailed descriptions of the preparation of certain polyhydric alcohol 3-alkylthiopropionate stabilizers by a process according to this invention.

EXAMPLE 1

Synthesis of pentaerythritol tetrakis(3-laurylthiopropionate).

40.3 g (0.24 mole) of dodecene-1, 21.2 g (0.2 mole) of 3-mercaptopropionic acid, 6.8 g (0.05 mole) of pentaerythritol, 0.68 g of p-toluenesulfonic acid and 0.07 g of azobisisobutyronitrile were put into a flask and heated with stirring at 80° C. in an atmosphere of nitrogen for four hours. The resulting water and an excess of dodecene-1 were vacuum-distilled off. After cooling, toluene was added, and the solution washed with water and then with 10% of NaHCO₃ aqueous solution. After drying, toluene was removed. 54.9 g (yield 94.7%) of white powder having M.P. 44°–47° C. was obtained by adding methanol and collecting the crystalline product.

EXAMPLE 2

Synthesis of pentaerythritol tetrakis(3-stearyl-thiopropionate)

52.9 g (0.21 mole) of octadecene-1, 21.2 g (0.2 mole) of 3-mercaptopropionic acid, 6.8 g (0.05 mole) of pentaerythritol, 0.75 g of p-toluene-sulfonic acid and 0.75 g of lauroylperoxide were put into a flask and heated with stirring at 110° C. for five hours. 75 ml of toluene was added and further heated under stirring at the reflux temperature for two hours. After cooling the mixture was washed with water and 10% NaHCO₃ aqueous solution. After drying, the solvent was removed under vacuum. 70.1 g (yield 93.7%) of white powder having M.P. 64.0°–66.0° C. -as obtained by adding isopropyl alcohol and collecting the crystalline product.

EXAMPLE 3

Synthesis of tris(2-hydroxyethyl)isocyanurate tris(3-$C_{12-14}$ alkylthiopropionate) 43.4 g (0.24 mole of mixed alpha-olefin ($C_{12-14}$, DIALEN 124: Mitsubishi Chemical), 24.0 g (0.2 mole) of 3-mercaptopropionic acid methyl ester, 17.5 g (0.67 mole) of tris(2-hydroxyethyl) isocyanurate, 0.8 g of sodium methoxide and 0.08 g of azobisisobutyronitrile were put into a flask and heated with stirring at 80° C. in an atmosphere of nitrogen for three hours and further at 100° C. for five hours. The resulting methanol and an excess of alpha-olefin were vacuum-distilled off. After cooling, toluene was added, and the mixture washed with water, dried and stripped of toluene. 57.2 g (yield 91.2%) of white powder having M.P. 67°–69° C. was obtained by adding methanol, triturating and collecting the crystalline product.

EXAMPLE 4

Synthesis of pentaerythritol tetrakis(3-$C_{16-18}$ alkylthiopropionate)

53 g (0.5 mole) of 3-mercaptopropionic acid, 117.8 g (0.51 mole) of mixed alpha-olefin ($C_{16-18}$ Mitsubishi DIALEN 168), 17.0 g (0.125 mole) of pentaerythritol, 1.9 g of p-toluene-sulfonic acid, and 0.19 g of azobisisobutyronitrile were put into a flask and heated with stirring at 80° to 90° C. in an atmosphere of nitrogen for five hours. The resulting water was vacuum-distilled off. After cooling, toluene was added, the mixture washed with water and then with 10% NaHCO₃ aqueous solution, dried, and concentrated by distilling the toluene. 162.9 g (yield 92.3%) of white powder having M.P. 61.5°–54° C. was obtained by adding methanol to the highly concentrated residue and collecting the crystalline product.

EXAMPLE 5

Synthesis of tris(2-hydroxyethyl)isocyanurate tris(3-stearylthiopropionate)

172.3 g (0.33 mole) of 1-octadecene, 31.8 g (0.3 mole) of 3-mercaptopropionic acid, 26.1 g (0.1 mole) of tris (2-hydroxyethyl)isocyanurate, 0.23 g of azobisisobutyronitrile and 2.3 g. of p-toluenesulfonic acid were put into a flask and heated with stirring at 80° C. in an atmosphere of nitrogen for five and one half hours. The resulting water and an excess of octadecene were vacuum-distilled off. After cooling, toluene addition, water-washing, drying and removing toluene, 118.2 g (yield 92.3%) of white powder having M.P. 74.5°–76.5° C. was obtained by adding methanol to the residue and collecting the solid product.

EXAMPLE 6

Synthesis of pentaerythritol tetrakis (3-$C_{20-24}$ alkylthiopropionate)

63.2 g (0.21 mole) of $C_{20-24}$ alpha-olefin mixture, 6.8 g (0.05 mole) of pentaerythritol, 21.2 g (0.2 mole) of 3-mercaptopropionic acid, 0.9 g of p-toluene sulfonic acid and 0.9 g of t-butyl peroxyneodecanoate were put into a flask and heated with stirring at 110°–115° C. in an atmosphere of nitrogen for three hours. 0.45 g of t-butyl peroxyneodecanoate was added and further reacted for three hours. After cooling, toluene addition, water-washing, drying and solvent removal, 73.9 g (yield 87.4%) of white powder having M.P. 66°–68° C. was obtained by recrystallization from heptane.

COMPARATIVE EXAMPLE

Synthesis of pentaerythritol tetrakis (3-laurylthiopropionate) U.S. Pat. No. 3,758,549

123 g (0.6 mole) of n-laurylmercaptan and 0.5 g of sodium methoxide were put into a flask, and while maintaining the temperature at 25° to 30° C., 86.1 g (1.0 mole) of methyl acrylate was added dropwise over the period of approximately fifty minutes. After completion of the addition, the mixture was further stirred at 25° to 30° C. for seventeen hours and then subjected to vacuum distillation to obtain 122.3 g (yield 70.8%) of methyl beta-laurylthiopropionate. The distillation temperature was 152° to 153.5° C./0.3 to 0.4 mm Hg.

57.6 g (0.2 mole) of the obtained ester, 6.8 g (0.05 mole) of pentaerythritol and 0.25 g of sodium methoxide were put into a flask and heated with stirring at 100°–110° C. in an atmosphere of nitrogen for seven hours, after cooling, toluene was added and the solution passed through a bed of alumina. The toluene was removed and 55.4 g (yield 95.5%) of white powder having M.P. 47°–49° C. was obtained by adding methanol and collecting the crystalline product.

Total yield: 67.6% for the two steps.

Polyolefin resins that can be stabilized with polyhydric alcohol 3-alkylthiopropionates prepared by a process of this invention include polymers of olefins having two to six carbon atoms such as polyethylene, polypropylene, poly-1-butene, poly-3-methylbutene, poly-4-methylpentene, poly-1-hexane, and copolymers of these olefins, particularly copolymers of ethylene with propylene, butene-1, of hexene-1, as well as blends of two or more of these polyolefins, and alpha-olefin copolymers such as ethylene-vinylacetate copolymers, ethylene-ethyl acrylate copolymers, and ethylene-propylene-diene terpolymers. They also include olefin resins and copolymers crosslinked by heating with a peroxide or by exposure to ionizing radiation, and foamed poly-olefins which are foamed by a blowing agent.

Stabilizer compositions comprising a polyhydric alcohol 3-alkylthiopropionate prepared by a process of this invention together with a polyolefin resin stabilizer such as a phenol, an organic phosphite, and/or alkaline earth metal salt of a monocarboxylic acid having 6 to 24 carbon atoms can be formulated and marketed in liquid, solid and paste forms. An inert solvent can be used to facilitate handling. The components can also be formulated as a uniform mixture by heating together until a homogeneous melt is formed, at temperatures up to about 160° C. for one to four or more hours if necessary, and allowed to solidify and subdivided by grinding or flaking.

A stabilizer prepared according to this invention is added to the polyolefin resins such as mentioned above to improve their oxidative stability in an amount of 0.01 to 5 weight parts, preferably 0.05 to 3 weight parts, per 100 weight parts of the resins.

Incorporation of a phenol in the stabilizer composition of this invention produces an excellent synergistic effect enhancing the effectiveness of the polyhydric alcohol 3-alkylthiopropionate stabilizer.

Representative phenols include, for example, 2,6-di-t-butyl-p-cresol, 1,1,3-tris(2-methyl-4-hydroxy-5-t-butyl-phenyl)butane, n-octadecyl 3-(3',5'-di-t-butyl-4'- hydroxyphenyl)propionate, and 1,3,5-tris (3',5'-di-t-butyl-4'-hydroxybenzyl)isocyanurate. A comprehensive disclosure of phenols by M. Minagawa, U.S. Pat. No. 3,997,551, column 19 line 27 to column 25 line 68 is here incorporated by reference.

Representative organic phosphites include triisodecyl phosphite, tri-n-octadecyl phosphite, phenyl di-2-ethylhexyl phosphite, and di-n-octadecyl pentaerythritol diphosphite. A comprehensive disclosure of useful organic phosphites by M. Minagawa, U.S. Pat. No. 3,997,551, column 15 line 63 to column 19 line 26 is here incorporated by reference.

Representative alkaline earth metal salts of monocarboxylic acids having 6 to 24 carbon atoms include calcium 2-ethylbutyrate, strontium caproate, barium benzoate, calcium-p-t-butylbenzoate, strontium laurate, barium myristate, calcium palmitate, strontium behenate, and barium linoleate. Additional alkaline earth metal salts of monocarboxylic acids having 6 to 24 carbon atoms are included among those disclosed by M. Minagawa in U.S. Pat. No. 3,869,423, column 9 line 56 to column 20 line 35. The concentration of alkaline earth metal salt based on 100 parts of polyolefin resin can range from zero to about 1 part by weight.

The preparation of stabilized polyolefin resin compositions according to this invention is easily accomplished by conventional procedures. A heated two roll mill, for example, is a convenient compounding tool for blending stabilizer compositions of the invention with polyolefin resins.

EXAMPLE 7

Unstabilized polypropylene resin (Profax 6501) 100 parts by weight, Ca-stearate 0.2 part, pentaerythritol tetrakis-beta-(3,5-di-t-butyl-4-hydroxyphenyl) propionate 0.1 part and sample compound 0.3 part were compounded by grinding and mixing 10 minutes. The compounded mixture was kneaded on a two roll mill at 180° C. for 6 minutes to give a rough sheet and then a polished sheet of 1.0 mm in thickness was prepared by compression molding at 180° C., and 200 kg/cm² for 5 minutes. Test pieces of 10×20 mm were cut off from this sheet and a heat aging test was carried out on aluminum foils in a Geer oven at 160° C. in an air atmosphere. Also, the color of the sheets after 64 hours exposure to fluorescent light was measured as yellowness fraction by Hunter Colorimeter. The results are shown in Table-1.

TABLE 1

| NO. | SAMPLE COMPOUND | 160° C. Oven Beginning Time of Deterioration hrs. | 64 hour Light Exposure Yellowness |
|---|---|---|---|
| Control | | | |
| 7-1 | Dilaurylthiopropionate | 680 | 0.16 |
| 7-2 | Pentaerythritol tetrakis(3-laurylthiopropionate) of Comparative Example | 1390 | 0.10 |
| Example | | | |
| 7-1 | Pentaerythritol tetrakis(3-laurylthiopropionate) of Example 1 | 1420 | 0.08 |
| 7-2 | Pentaerythritol tetrakis(3-stearylthiopropionate) of Example 2 | 1370 | 0.10 |
| 7-3 | T.H.E.I.C. tris(3-alkylthiopropionate) of Example 3* | 1330 | 0.10 |
| 7-4 | Pentaerythritol tetrakis(3-C₁₆₋₁₈ alkylthiopropionate) of Example 4 | 1400 | 0.09 |
| 7-5 | T.H.E.I.C. tris(3-stearyl- | | |

TABLE 1-continued

| NO. | SAMPLE COMPOUND | 160° C. Oven Beginning Time of Deterioration hrs. | 64 hour Light Exposure Yellowness |
|---|---|---|---|
| | thiopropionate) of Example 5* | 1350 | 0.09 |
| 7-6 | Pentaerythritol tetrakis (3-C₂₀₋₂₄ alkylthiopropionate) of Example 6 | 1340 | 0.10 |

*T.H.E.I.C. = tris(2-hydroxyethyl)isocyanurate

The results of these tests show that polyhydric alcohol 3-alkylthiopropionate stabilizers prepared by a process of this invention are far superior in effectiveness to a standard commercial thiodipropionate and equal or better when compared to a polyhydric alcohol 3-alkylthiopropionate made by a conventional process of synthesis.

We claim:

1. A process for preparing a polyhydric alcohol 3-alkylthiopropionate polyolefin stabilizer capable of enhancing the resistance to deterioration and minimizing the formation of undesirable color and odor of a polyolefin resin when heated at 150° C., comprising the step of heating a reaction mixture containing at least one polyhydric alcohol having 3 to 6 alcoholic hydroxyl groups and 3 to 20 carbon atoms, provided that the number of carbon atoms is at least equal to the number of alcoholic hydroxyl groups, and for each mole of alcoholic hydroxyl group supplied by the polyhydric alcohol from 0.6 to 1.5 moles of a betamercaptopropionic acid compound selected from the group consisting of betamercaptopropionic acid and a lower alkyl ester thereof and from 0.6 to 2 moles of at least one alpha-olefin having 6 to 40 carbon atoms, and an amount effective to initiate reaction of a reaction initiator selected from the group consisting of azonitriles and organic peroxides having 4 to 40 carbon atoms, and subsequently recovering the polyhydric alcohol 3-alkylthiopropionate polyolefin resin stabilizer from the mixture.

2. A process according to claim 1 in which the beta-mercaptopropionic acid compound is beta-mercaptopropionic acid.

3. A process according to claim 1 in which the beta-mercaptopropionic acid compound is methyl beta-mercaptopropionate.

4. A process according to claim 1 in which the reaction initiator is an aliphatic diacyl peroxide having 4 to 40 carbon atoms.

5. A process according to claim 4 in which the reaction initiator is lauroyl peroxide.

6. A process according to claim 1 in which the reaction initiator is 2,2'-azobis(2-methylpropionitrile).

7. A process according to claim 1 in which the polyhydric alcohol is pentaerythritol.

8. A process according to claim 1 in which the polyhydric alcohol is tris(2-hydroxyethyl)isocyanurate.

9. A process according to claim 1 in which the reaction mixture contains as an additional ingredient a catalytically effective amount of an esterification catalyst selected from the group consisting of cation exchange resins, organic sulfonic acids, inorganic acids, organotin compounds, and metal alkoxides.

10. A process according to claim 3 in which the reaction mixture contains as an added ingredient a catalytically effective amount of a basic esterification catalyst.

11. A process according to claim 1 in which the polyhydric alcohol 3-alkylthiopropionate resin stabilizer is recovered by the use of a solvent combination comprising an aromatic hydrocarbon and a lower aliphatic alcohol.

12. A process according to claim 11 in which the aromatic hydrocarbon is toluene and the aliphatic alcohol is methanol.

* * * * *